US008329169B2

(12) United States Patent
Fung et al.

(10) Patent No.: US 8,329,169 B2
(45) Date of Patent: Dec. 11, 2012

(54) METHODS AND COMPOSITIONS FOR THE PREVENTION AND TREATMENT OF SEPSIS

(75) Inventors: Sek Chung Fung, Houston, TX (US); Tom Eirik Mollnes, Bodø (NO)

(73) Assignee: Genentech, Inc., San Francisco, CA (US)

( * ) Notice: Subject to any disclaimer, the term of this patent is extended or adjusted under 35 U.S.C. 154(b) by 782 days.

(21) Appl. No.: 10/556,998

(22) PCT Filed: May 14, 2004

(86) PCT No.: PCT/US2004/015135
§ 371 (c)(1),
(2), (4) Date: May 23, 2006

(87) PCT Pub. No.: WO2004/103294
PCT Pub. Date: Dec. 2, 2004

(65) Prior Publication Data
US 2007/0274989 A1    Nov. 29, 2007

Related U.S. Application Data

(60) Provisional application No. 60/470,681, filed on May 15, 2003.

(51) Int. Cl.
*A61K 39/395* (2006.01)
*A61K 39/00* (2006.01)
(52) U.S. Cl. ............. 424/130.1; 424/131.1; 424/136.1
(58) Field of Classification Search ............ None
See application file for complete search history.

(56) References Cited

U.S. PATENT DOCUMENTS

| 5,730,980 | A |   | 3/1998  | Ulevitch et al. |
|-----------|---|---|---------|-----------------|
| 5,804,189 | A |   | 9/1998  | Goyert |
| 5,820,858 | A |   | 10/1998 | Letureq et al. |
| 6,045,795 | A |   | 4/2000  | Ulevitch et al. |
| 6,168,790 | B1 |  | 1/2001  | Ulevitch et al. |
| 6,169,068 | B1 |  | 1/2001  | Levin et al. |
| 6,297,049 | B1 |  | 10/2001 | Ulevitch et al. |
| 6,315,999 | B1 | * | 11/2001 | Sadoff et al. ............ 424/145.1 |
| 6,495,332 | B2 |  | 12/2002 | Ulevitch et al. |
| 6,881,408 | B1 |  | 4/2005  | Henreich et al. |
| 2001/0022969 | A1 |  | 9/2001 | Ulevitch et al. |
| 2002/0034509 | A1 |  | 3/2002 | Ulevitch et al. |
| 2002/0044929 | A1 | * | 4/2002 | Fisher et al. ............ 424/94.63 |
| 2002/0165138 | A1 | * | 11/2002 | Ward et al. ............ 514/12 |
| 2003/0077576 | A1 | * | 4/2003 | Trial et al. ............ 435/5 |
| 2003/0103969 | A1 |  | 6/2003 | Ulevitch et al. |
| 2003/0114377 | A1 |  | 6/2003 | Kirkland et al. |
| 2004/0091478 | A1 |  | 5/2004 | Furusako et al. |
| 2004/0092712 | A1 |  | 5/2004 | Furusako et al. |
| 2004/0259795 | A1 |  | 12/2004 | Julius et al. |

FOREIGN PATENT DOCUMENTS

| CA | 2072626 | 3/1992 |
| CA | 2072626 | 4/1992 |
| CA | 2366455 | 5/2000 |
| EP | 0245993 | 11/1987 |
| EP | 0 245 993 | 5/1993 |
| EP | 0911400 A1 | 4/1999 |
| JP | 62-269699 A | 11/1987 |
| JP | 05-501399 | 3/1993 |
| JP | 05-502893 A | 5/1993 |
| JP | 10-130167 | 5/1993 |
| JP | 08-511506 A | 12/1996 |
| JP | 10-505839 A | 6/1998 |
| JP | 2002-539910 | 11/2002 |
| WO | WO 91/01639 A1 | 2/1991 |
| WO | WO 92/04908 A1 | 4/1992 |
| WO | WO 93/19772 A1 | 10/1993 |
| WO | WO 94/17822 | 8/1994 |
| WO | WO 94/28025 A1 | 12/1994 |
| WO | WO 96/08272 | 3/1996 |
| WO | WO 9608272 A1 | 3/1996 |
| WO | WO 98/39438 | 11/1998 |
| WO | WO 99/61468 A2 | 12/1999 |
| WO | WO 01/15731 A1 | 3/2001 |
| WO | WO 01/72993 | 10/2001 |
| WO | WO 02/42333 | 5/2002 |
| WO | WO 03/015819 A2 | 2/2003 |
| WO | WO 2004/075837 A2 * | 9/2004 |

OTHER PUBLICATIONS

Definition of kit from Compact Oxford English Dictionary at http://www.askoxford.com/concise_oed/kit_1?view=uk retrieved Apr. 30, 2009.*
Wang et al. Shock. vol. 20(5), Nov. 2003, pp. 402-414.*
Definition of Extracorporeal Route of Drug administration: http://ncicb.nci.nih.gov/xml/owl/EVS/Thesaurus.owl#Extracorporeal_Circulation_Route_of_Drug_Administration, retrieved Jul. 26, 2010—printout of 4 pages.*
Listing of Routes of Drug administration:http://bioportal.bioontology.org/visualize/40377/Intraocular_Route_of_Drug_Administration, retrieved Jul. 26, 2010—printout of 2 pages.*
Holliger et al. PNAS vol. 90, pp. 6444-6448, Jul. 1993.*
Papo et al. (JBC 280, 10378-10387, 2005).*
Weighardt, H., et al., Cutting Edge: Myeloid Differentiation Factor 88 Deficiency Improves Resistance Against Sepsis Caused by Polymicrobial Infection, Journal of Immunology, 2002, vol. 169, pp. 2823-2827.
Dobrovolskaia, M., et al., Toll Receptors, CD14, and Macrophage Activation and Deactivation by LPS, Microbes and Infection, 2002, vol. 4, pp. 903-914.
Ulevitch, R., et al., New Therapeutic Targets Revealed Through Investigations of Innate Immunity, Crit Care Med, 2001, vol. 29, No. 7 (Suppl.), pp. S8-S12.

(Continued)

*Primary Examiner* — Oluwatosin Ogunbiyi
(74) *Attorney, Agent, or Firm* — Jones Day

(57) ABSTRACT

The present invention includes compositions comprising one or more complement inhibitors and one or more CD14 pathway inhibitors for the prevention or treatment of sepsis. The complement inhibitors may be antibodies that bind to and inhibit complement proteins such as C5a and the CD14 pathway inhibitors may be antibodies that bind to and inhibit CD14 pathway components, such as CD14 and LPS. The invention also relates to methods of treating subjects suffering from sepsis comprising administering these compositions, as well as kits for supplying the compositions for treatment.

13 Claims, No Drawings

OTHER PUBLICATIONS

Supajatura, V., et al., Protective Roles of Mast Cells Against Enterobacterial Infection Are Mediated by Toll-Like Receptor 4, Journal of Immunology, 2001, vol. 167, pp. 2250-2256.

Marshall, J., Such Stuff as Dreams Are Made on: Mediator-Directed Therapy in Sepsis, Nature Reviews (Drug Discovery), 2003, vol. 2, pp. 391-405.

Poltorak, A., et al., Defective LPS Signaling in C3H/HeJ and C57BL/10ScCr Mice: Mutations in *Tlr4* Gene, Science, 1998, vol. 282, pp. 2085-2088.

Riedemann, N., et al., Novel Strategies for the Treatment of Sepsis, Nature Medicine, 2003, vol. 9, No. 5, pp. 517-524.

Nagai, Y., et al., Essential Role of MD-2 in LPS Responsiveness and TLR4 Distribution, Nature Immunology, 2002, vol. 3, No. 7, pp. 667-672.

Muzio, M., et al., Toll-Like Receptors, Microbes and Infection, 2000, vol. 2, pp. 251-255.

Miyake, K., Innate Recognition of Lipopolysaccharide by CD14 and Toll-Like Receptor 4-MD-2: Unique Roles for MD-2, International Immunopharmacology, 2003, vol. 3, pp. 119-128.

Guha, M., et al., LPS Induction of Gene Expression in Human Monocytes, Cellular Signalling, 2001, vol. 13, pp. 85-94.

Lien, E., et al., Toll-Like Receptor 4 Imparts Ligand-Specific Recognition of Bacterial Lipopolysaccharide, Journal of Clinical Investigation, 2000, vol. 105, No. 4, pp. 497-504.

Landmann, R., et al., CD14, New Aspects of Ligand and Signal Diversity, Microbes and Infection, 2000, vol. 2, pp. 295-304.

Henneke, P., et al., Novel Engagement of CD14 and Multiple Toll-Like Receptors by Group B *Streptococci*, Journal of Immunology, 2001, vol. 167, pp. 7069-7076.

Henneke, P., et al., Innate Immune Recognition of Lipopolysaccharide by Endothelial Cells, Crit Care Med, 2002, vol. 30, No. 5 (Suppl.), pp. S207-S213.

Heumann, D., et al., Molecular Basis of Host-Pathogen Interaction in Septic Shock, Current Opinion in Microbiology, 1998, vol. 1, pp. 49-55.

Beutler, B., et al., Sepsis and Evolution of the Innate Immune Response, Crit Care Med, 2001, vol. 29, No. 7 (Suppl.), pp. S2-S7.

Antal-Szalmas, P., Evaluation of CD14 in Host Defense, European Journal of Clinical Investigation, 2000, vol. 30, pp. 167-179.

Andonegui, G., et al., Endothelium-Derived Toll-Like Receptor-4 is the Key Molecule in LPS-Induced Neutrophil Sequestration into Lungs, Journal of Clinical Investigation, 2003, vol. 111, No. 7, pp. 1011-1020.

Huber-Lang Markus S et al., Protection of innate immunity by C5aR antagonist in septic mice FASEB Journal, vol. 16, No. 12, Oct. 2002, pp. 1567-1574.

Leturcq Didier J et al., "Antibodies against CD14 protect primates from endotoxin-induced shock" Journal of Clinical Investigation, vol. 98, No. 7, 1996, pp. 1533-1538.

Mollnes Tom Eirik et al., "Essential role of the C5a receptor in *E. coli*-induced oxidative burst and phagocytosis revealed by a novel lepirudin-based human whole bood model of inflammation" Blood, vol. 100, No. 5, Sep. 1, 2002, pp. 1869-1877.

Mollnes et al. "Inhibition of andotoxin-induced oxidative bust by the C3 bringing peptide compstatin in a novel whole blood model of inflammation" Immunopharmacology vol. 49, No. 1-2, Aug. 2000, p. 62.

Brekke et al., "Combined inhibition of complement and CD14 abolish *E. coli*-induced cytokine-, chemokine- and growth factor-synthesis in human whole blood", *Molecular Immunology*, 45 (2008) 3804-3813.

Yamaguchi et al, 1995, Clinical study on AIDS and opportunistic infections, A research report in Japan, 1996: 95-101.

* cited by examiner

METHODS AND COMPOSITIONS FOR THE PREVENTION AND TREATMENT OF SEPSIS

This application claims priority to U.S. Provisional Application No. 60/470,681, filed on 15 May 2003.

BACKGROUND OF THE INVENTION

1. Field of the Invention

This invention relates generally to methods and compositions for the prevention and treatment of sepsis and particularly to the use of a combination of complement inhibitors and CD14 pathway inhibitors to prevent or treat sepsis.

2. Description of the Prior Art Complement

The immune system protects the body against pathogenic bacteria, viruses, parasites and other harmful organisms. The immune system is divided into two components, the humoral system and the cellular system. Generally, the humoral system includes the complement system and the production of antibodies to defend against pathogens. The complement system, or simply complement, involves the production of proteins that assist the antibodies in the host defense. Complement is a group of at least 30 surface-bound and soluble proteins. The activity of the soluble proteins is destroyed by heating serum at 56° C. for 30 minutes. Complement proteins are involved in the opsonization of microorganisms for phagocytosis, direct killing of microorganisms by lysis, chemotactic attraction of leukocytes to sites of inflammation, activation of leukocytes, and processing of immune complexes.

Complement proteins work in a cascade wherein the binding of one protein promotes the binding of the next protein in the cascade. Activation of the cascade leads to release of biologically active small peptides called anaphylatoxins (C3a, C4a, and the most potent C5a) contributing to the inflammatory reaction, and eventually in the formation of a membrane attack complex (C5b-9 or MAC) that may lyse the target cell. Different complement molecules are synthesized by different cell types, e.g. fibroblasts and intestinal epithelial cells make C1, while most of the components are synthesized in the liver.

The components and mechanism of the complement system are well known. Basically, there are three complement pathways, the classical pathway, the lectin pathway, and the alternative pathway. The classical pathway is triggered primarily by immune complexes containing antigen and IgG or IgM, but also by other agents like C-reactive protein. The lectin pathway is triggered by binding of mannose binding lectin (MBL) or ficolins to carbohydrate structures (e.g. mannan) on foreign surfaces. The alternative pathway is activated principally by repeating polysaccharides and other polymeric structures such as those found on bacteria.

The classical pathway is activated when the globular domains of C1q (part of the C1qrs complex) bind to the Fc fragments of IgM or multiple molecules of IgG. In the presence of calcium ions, this binding causes the autocatalytic activation of two C1r molecules. The C1r molecules activate two molecules of C1s. C1s is a serine protease that cleaves C4a from C4b. C4b immediately binds to adjacent proteins or carbohydrates on the surface of the target cell and then binds to C2 in the presence of magnesium ions. C1s cleaves C2b from this complex, yielding the classical pathway C3 convertase, C4b2a The C3 convertase cleaves many hundreds of molecules of C3 into C3a and C3b. Some molecules of C3b will bind back to C4b2a to yield the classical pathway C5 convertase, C4b2a3b. C5 convertase cleaves C5 into C5a and C5b. C5b binds to the surface of the cell, initiating the formation of MAC.

C3a, C4a, and C5a are all anaphylatoxins. C3a and C5a are also chemoattractants. C3a and C5a have the ability to bind to mast cells and basophils. C5a is also a potent activator of neutrophils, basophils and macrophages and causes induction of adhesion molecules on vascular endothelial cells. C5a also down regulates neutrophils and monocytes. When C3a and C5a bind their receptors on the mast cells and basophils, these cells release histamine and other highly active peptides into blood and tissues. These peptides increase the permeability of the vascular walls allowing neutrophils to migrate into the area Neutrophils are further encouraged to migrate to the site of complement activation due to the potent chemotactic (attractant) effect of C5a. The neutrophils phagocytose invading pathogens and also release mediators that attract macrophages to the site of infection. These cells also have the ability to phagocytose invading cells and further promote the inflammatory response and effectively eliminate many of the infections microorganisms.

The "lectin pathway" is similar to the classical pathway except it is initiated by the calcium-dependent lectin MBL that binds to terminal mannose groups on the surface of bacteria. MBL is analogous to C1q. When MBL binds to its target, it releases and thus activates three associated serine proteases known as MASP1, MASP2 and MASP3 (mannose-binding lectin-associated serine protease), which are analogous to C1r and C1s. Among them, MASP2 plays the key role in cleaving C4 into C4b and C4a and C2 into C2b and C2a Following the activation of C4 and C2, the lectin pathway is identical to the classical pathway.

The alternative complement pathway involves an amplification loop utilizing C3b produced by the classical pathway. Some molecules of C3b generated by the classical pathway C3 convertase are funneled into the alternative pathway. Surface-bound C3b binds Factor B to yield C3bB, which becomes a substrate for Factor D. Factor D is a serine protease that cleaves the Ba fragment, leaving C3bBb bound to the surface of the target cell. C3bBb is stabilized by properdin (P), forming the complex C3bBbP, which acts as the alternative pathway C3 convertase. As in the classical pathway, the C3 convertase participates in an amplification loop to cleave many C3 molecules, resulting in the deposition of C3b molecules on the target cell. Some of these C3b molecules bind back to C3bBb to form C3bBb3b, the alternative pathway C5 convertase. C5 convertase cleaves C5 into C5a and C5b. C5b binds to the surface of the cell to initiate the formation of the membrane attack complex.

The classical, lectin, and alternative pathways all end with the formation of C5 convertase. C5 convertase leads to the assembly of the MAC via the lytic pathway. Components C5-C8 attach to one another in tandem and promote the insertion of one or more monomers of C9 into the lipid bilayer of the target cell. This insertion leads to the formation of pores that cause calcium influx with subsequent cellular activation of nucleated cells or cell lysis and death if the attack is sufficiently strong.

The CD14 Pathway

CD14 is a 53 kD glycophosphatidylinositol (GPI)-linked glycoprotein and functions as high affinity endotoxin (LPS) receptor on the surface of monocytes, macrophages, and granulocytes. Since CD14 is a GPI-linked protein it has no transmembrane or intracellular part that can transmit signals. CD14 is also present in a soluble form in human serum and other body fluids. Soluble CD14 (sCD14) is directly secreted or derived from protease-dependent shedding of the membrane bound molecule. sCD14 competes with membrane bound CD14 (mCD14) for LPS binding and is able to neutralize LPS-induced responses in vitro and in vivo. sCD14 mediates the LPS-induced activation of non-CD14-expressing endothelial, epithelial, and smooth-muscle cells. LBP (lipopolysaccharide binding protein) is a 58 kD acute phase glycoprotein and binds to the lipid A portion of LPS with high affinity and catalyzes the CD14-dependent cellular activation by LPS. MD2 is a secreted accessory protein that binds to the extracellular domain of toll-like receptor TLR4 and facilitates LPS responsiveness, possibly by stabilizing TLR4 dimers. The CD14/MD2/TLR4 complex appears to be the major, and possibly the exclusive, receptor for LPS isolated from most gram-negative organisms.

The CD14 pathway is known to be important in the prevention and treatment of sepsis and anti-CD14 antibodies are known to attenuate sepsis via the CD14 pathway, e.g., Letureq D J, J Clin Invest 1996 Oct. 1; 98(7):1533-8 and U.S. Pat. Nos. 6,495,332 and 6,297,049. The CD14 pathway comprises several steps. Generally, LPS from the outer membrane of gram-negative bacteria initiates the sequence in the pathway by forming a complex with LPS binding protein (LBP) in plasma The LPS-LBP complex transfers the LPS monomer to CD14 in the phagocyte cell membrane. CD14 and MD2 promote the binding of LPS to TLR4 which signals the cell interior. Binding of LPS by TLR4 recruits the adaptor molecule MyD88 to the cytoplasmic domain of the receptor and MyD88 then binds to tumor necrosis factor receptor associated factor 6 (TRAF6). TRAF6 binds the serine-threonine kinase IRAK. The TRAF6/IRAK complex is believed to activate the phosphorylation of the two subunits of the NFκB kinase (NIK) and cause them to form a heterodimer, IκB kinase (IKK). The IKK dimer then phosphorylates IκB and causes it to dissociate from NFκB. NFκB then can migrate to the nucleus, bind to DNA, and activate the transcription of genes encoding inflammatory mediators.

Sepsis

Sepsis is a disease characterized by an overwhelming systemic inflammatory response to infection. Bacterial sepsis is a complex systemic inflammatory syndrome caused by aggressive bacterial infection in the blood. Sepsis causes high morbidity and mortality in humans and other animals. In the United States, sepsis is a leading cause of nosocomial death for humans (particularly in intensive care units) and death from infections in young livestock and other animals. Each year, over 700,000 new cases of sepsis are diagnosed in humans. Extrapolated to a global population, this represents several million cases of severe sepsis worldwide annually. Mortality rates range from about 20-30% and represent at least 150,000 deaths per year in the United States.

Sepsis can result from many causes but is typically triggered by events such as pneumonia, trauma, surgery, and burns or by conditions such as cancer or AIDS. Sepsis usually begins with tremor, fever, falling blood pressure (septic shock), rapid breathing, rapid heart rate, and skin lesions. Within hours, sepsis may cause spontaneous clotting in blood vessels, severe hypotension, multiple organ failure, shock, and eventually death. Typically, these symptoms are caused by the excessive or uncontrolled activation of host defense mechanisms such as cytokines, leukocytes, and complement.

Sepsis is usually caused by bacterial infections (either Gram-negative or Gram-positive bacteria) but can also be caused by other pathogens such as fungi, viruses, and parasites and non-infective stimuli such as superantigens. Most often however, sepsis is caused by Gram-negative bacteria infections. However, the injury and symptoms attributable to sepsis are not only caused by the bacteria but are also caused by a component of the bacteria cell wall known as endotoxin or lipopolysaccharide (LPS). LPS molecules are glycolipids that are ubiquitous in the outer membrane of all Gram-negative bacteria While the known chemical structure of the LPS molecule is complex and diverse, a common feature is the lipid A region. Recognition of the highly conserved lipid A LPS region initiates many, if not all, of the events responsible for sepsis. LPS is released when the immune system destroys the invading bacteria The released LPS binds to monocytes, macrophages, and endothelial cells and triggers the production of various mediators such as tumor necrosis factor-alpha (TNFα) and interleukins (IL-1, IL-6, and IL-8). Production of excessive TNF-α, IL-1, IL-6, and IL-8 is a major cause of sepsis.

Known methods for treating sepsis include antibacterials, antibodies, small molecules and peptides, protein C, supportive therapy with oxygen, intravenous fluids, and medications that increase blood pressure. For example, US Patent Application No. 20030021783 discloses using anti-IL-8 antibodies for the treatment of sepsis, US Patent Application No. 20030008822 discloses using anti-IL18 antibodies for the treatment of sepsis, US Patent Application No. 20020165138 discloses using anti-C5a antibodies and C-terminal truncated C5a peptides for the prevention and treatment of sepsis in animals, US Patent Application No. 20020155094 discloses using chemokines and chemokine fragments for treating sepsis, US Patent Application No. 20020044929 discloses using a combination of protein C and BPI protein for treating sepsis, US Patent Application No. 20020034509 discloses using anti-CD14 antibodies for the treatment of sepsis, and US Patent Application No. 20020006915 discloses using COX-2 inhibitors to treat sepsis. Similarly, U.S. Pat. No. 6,534,648 discloses using algae lipopolysaccharides to combat sepsis, U.S. Pat. Nos. 6,495,332 and 6,297,049 discloses using anti-CD14 antibodies to treat sepsis, U.S. Pat. No. 6,489,296 discloses using protein C to reduce the mortality in a human patient with severe sepsis, U.S. Pat. No. 6,344,197 discloses using a synergistic combination therapy that combines protein C and BPI to treat sepsis. The patent does not disclose using a combination of compounds from both the complement and the CD14 pathway, U.S. Pat. No. 6,315,999 discloses using an antibody to tumor necrosis factor-α (anti-TNFα) and an antibody to bacterial lipopolysaccharide (anti-LPS) together to treat sepsis. The patent does not disclose using a combination of compounds from both the complement and the CD14 pathway, U.S. Pat. No. 6,063,764 a method for prophylactically or therapeutically treating sepsis or septic shock using lipoprotein associated coagulation inhibitor, U.S. Pat. No. 6,042,821 discloses a method of preventing and treating sepsis using chemokines, U.S. Pat. No. 5,354,771 discloses a method for treating sepsis using a keto analog of a branched-chain amino acid, and U.S. Pat. No. 5,093,117 discloses pharmaceutical compositions useful for the treatment or prophylaxis of sepsis comprising polyclonal immunoglobulins against Gram-negative bacteria and a blood clot-dissolving effective amount of protein C.

However, despite the major advances of the past several decades in the treatment of serious infections, the incidence of sepsis and mortality due to sepsis continue to increase. There is, therefore, a need for new methods and compositions for the prevention and treatment of sepsis.

SUMMARY OF THE INVENTION

It is, therefore, an object of the present invention to provide methods and compositions for preventing and treating sepsis.

It is another object of the invention to decrease the morbidity and mortality caused by sepsis.

It is another object of the invention to provide a kit useful for preventing and treating sepsis.

These and other objects are achieved using a novel method for preventing or treating sepsis that comprises administering in conjunction a sepsis preventing or treating amount of a complement inhibitor and a sepsis preventing or treating amount of a CD14 pathway inhibitor to a patient likely to develop or suffering from sepsis. The complement inhibitor can be any known complement inhibitor but is preferably an antibody or a functionally equivalent fragment thereof that binds to and inhibits complement components. The CD14 pathway inhibitor can be any known CD14 pathway inhibitor but is preferably an antibody or a functionally equivalent fragment thereof that binds to and inhibits CD14.

Other and further objects, features and advantages of the present invention will be readily apparent to those skilled in the art.

DETAILED DESCRIPTION OF THE INVENTION

Definitions

The term "patient" means a human or other animal likely to develop or suffering from sepsis, including bovine, porcine, canine, feline, equine, avian, and ovine animals. Preferably, the patient is a human.

The term "in conjunction" means that the complement inhibitors and CD14 pathway inhibitors are administered to a patient at about the same time (1) separately at the same or different frequency using the same or different administration routes or (2) together in a pharmaceutically acceptable composition or (3) together as part of a bispecific antibody or fragment thereof, particularly those with a binding site for a complement component and another binding site for a CD14 pathway component. "About the same time" generally means that the inhibitors are administered at the same time or within about 72 hours of each other.

The term "parenterally" means administration by intravenous, subcutaneous, intramuscular, or intraperitoneal injection.

The term "functionally equivalent fragments" means antibody fragments that bind to components of the complement system or the CD14 pathway and inhibit complement activation or CD14 pathway function in substantially the same manner as the complete antibody.

The term "antagonist" means any molecule that blocks, prevents, inhibits, or neutralizes the normal function of a complement component or a CD14 pathway component. One type of antagonist is a molecule that interferes with the interaction between CD14 and its LPS ligand, including an antibody or antibody fragment.

This invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a," "an," and "the" include plural reference unless the context clearly dictates otherwise, e.g., reference to "a host cell" includes a plurality of such host cells.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, devices, and materials are described herein.

All patents and publications mentioned herein are incorporated herein by reference to the extent allowed by law for the purpose of describing and disclosing the compounds and methodologies reported therein that might be used with the present invention. However, nothing herein is to be construed as an admission that the invention is not entitled to antedate such disclosure by virtue of prior invention.

The Invention

In one aspect, the present invention provides a method for preventing and treating sepsis. The method comprises administering in conjunction a sepsis preventing or treating amount of one or more complement inhibitors and a sepsis preventing or treating amount of one or more CD14 pathway inhibitors to a patient. The invention is based upon the novel discovery that both the complement component of the immune system and the CD14 pathway play a critical role in the development of sepsis and that methods and compositions for inhibiting or preventing complement activation must be used in combination with methods and compositions for inhibiting the CD14 pathway to effectively prevent or treat sepsis. Using either complement inhibitors or CD14 pathway inhibitors alone will not effectively prevent or treat the disease. The methods and compositions are useful for decreasing the morbidity and mortality for patients susceptible to or suffering from sepsis.

The complement inhibitors of the present invention are any molecule known to inhibit complement activation in a patient. Generally, the complement inhibitors are small organic molecules, peptides, proteins, antibodies, antibody fragments, or other molecules that function as complement inhibitors. Useful complement inhibitors include compstatin and its functional analogs (inhibits C3), C1q inhibitors, C1 Inhibitor (covalently binds C1r and C1s), C1r inhibitors (binds and inhibits C1r), C1s inhibitors (binds and inhibits C1s), sCR1 and its analogues (dissociate all C3 convertases), anti-C5 antibodies (block C5 activation), anti-C5a and anti-C5a receptor antibodies and small-molecule drugs (inhibit C5a signaling pathway), anti-C3a and anti-C3a receptor antibodies and small-molecule drugs (inhibit C3a signaling pathway), anti-C6, 7, 8, or 9 antibodies (inhibit the formation or function of MAC), anti-Factor D antibodies (inhibits factor D cleaveage of factor B), anti-properdin antibodies (destabilize C3 and C5 convertases in the alternative pathway), Membrane Cofactor Protein (MCP) (cofactor for Factor I mediated C3b and C4b cleavage), Decay Accelerating Factor (DAF) (accelerates decay of all C3 convertases), and MCP-DAF fusion protein (CAB-2). Other useful inhibitors include C4bp (accelerates decay of classical pathway C3 convertase (C4b2a)), Factor H (accelerates decay of alternative pathway C3 convertase (C3bBb)), Factor I (proteolytically cleaves and inactivates C4b and C3b (cofactors are required)), Carboxypeptidase N (removes terminal arginine residues from C3a, C4a and C5a), vitronectin (S Protein) and clusterin (binds C5b-7 complex and prevents membrane insertion), and CD59 (inhibits lysis of bystander cells).

Preferably, the complement inhibitors are antibodies or functionally equivalent fragments thereof that bind to and inhibit one or more of the proteins that function in the complement cascade, e.g., C1, C2, C4, C3, C3a, C5, C5a, Factor D, factor B, properdin, MBL or their components, MASPs or their components, protease cleavage products and receptors. The antibodies bind to a selected complement protein in the complement cascade and inhibit or prevent complement activation when a patient is at risk for developing sepsis. In one embodiment, the complement inhibitor is an anti-C5 antibody or functionally equivalent fragment thereof that binds to C5 and inhibits the formation of C5a and C5b in the complement cascade. The antibody can also be an anti-C5a or anti-C5b antibody that binds to these proteins and inhibits their action in the complement cascade. Most preferably, the complement inhibitor is an anti-C5a antibody or functionally equivalent fragment thereof that binds to C5a and inhibits its action in the complement cascade. The antibodies can be a polyclonal or monoclonal antibodies but are preferably monoclonal antibodies.

In the preferred embodiment, the complement inhibitors are compounds that inhibit the anaphylatoxins in the complement cascade, particularly C5a Such inhibitors include anti-C3a antibodies and their functionally equivalent fragments, anti-C4a antibodies and their functionally equivalent fragments, and anti-C5a antibodies and their functionally equivalent fragments.

In another embodiment, the complement inhibitors are C5a receptor antagonists. These antagonists interfere with the interaction with C5a and its receptor and inhibit the function of the complement pathway. The C5a receptor antagonists include, but not limited to, F-[oPdChaWR] (Haynes D R et al, Biochem Pharmacol 2000; 60: 729-33; Huber-Lang M S et al., FASEB J 2002; 16: 1567-74)) and those described in WO0249993A2 and WO0249993A3.

The CD14 pathway inhibitors of the present invention are any molecule known to inhibit the CD14 pathway in a patient. Generally, the CD14 pathway inhibitors are small organic molecules, peptides, proteins, antibodies, antibody fragments, or other molecules that function as CD14 pathway inhibitors. Useful CD14 pathway inhibitors include CD14 pathway antagonists that interfere with the function of the CD14 pathway and the transcription of genes encoding inflammatory mediators. Such inhibitors include, but are not limited to, anti-CD14 pathway component antibodies such as anti-CD14 antibodies and anti-LPS antibodies that inhibit the action of a CD14 pathway component, LPS antagonists that bind to LPS and interfere with its binding to CD14, LBP antagonists that bind to LBP and interfere with its ability to transfer LPS to CD14, CD14 antisense nucleotides that interfere with the production of CD14, CD14 siRNAs that interfere with the production of CD14, and CD14 RNAi that interfere with the production of CD14.

In one embodiment, the CD14 pathway inhibitors are antibodies or functionally equivalent fragments thereof that bind to and inhibit one or more of the proteins that function in the CD14 pathway, e.g., LPS, lipopolysaccharide binding protein (LBP), CD14, TLR4, and MD2 for Gram negative sepsis and CD14, TLR2, and TLR6 for Gram positive sepsis. The anti-CD14 neutralizing monoclonal antibodies include, but not limited to, the antibody 4C1 described by Tasaka SI (Am J Respir Cell Mol Biol; 2003 Mar. 14, online publication ahead of print) and the antibody IC14 described by Axtelle T (J Endotoxin Res 2001; 7: 310-4). The antibodies bind to a selected protein in the pathway and inhibit or prevent membrane signaling and gene activation responsible for the production of unwanted cytokines. Preferably, the antibody is selected from the group consisting of anti-LPS antibodies, anti-LPB antibodies, anti-CD14 antibodies, anti-TLR4 antibodies, anti-MD2 antibodies, anti-TLR2 antibodies, anti-TLR6 antibodies, and functionally equivalent fragments thereof. Most preferably, the CD14 pathway inhibitor is an anti-CD14 antibody or functionally equivalent fragment thereof that binds to CD14 and inhibits membrane signaling and cytokine gene activation or an anti-LPS antibody that binds to LPS and prevents LPS from binding to CD14. The antibodies can be a polyclonal or monoclonal antibodies but are preferably monoclonal antibodies.

In another embodiment, the CD14 pathway inhibitors are anti-CD14 antibodies that have a change in the amino acid sequence in the anti-CD14 antibody constant regions, particularly CH2 and CH3 regions and most particularly in the Fc region. These "variant" anti-CD14 antibodies have an amino acid sequence that differs from its native counterpart by one or more amino acids, including modifications, substitutions, insertions, and deletions. These variants have altered amino acid sequences that alter the effector functions of the antibody Fc region, e.g., binding complement, binding to cell receptors on macrophages and monocytes, and the like. Preferably, such variant antibodies have a reduced ability to bind Fc receptors and/or to activate complement.

Methods for producing antibodies and their functionally equivalent fragments, including polyclonal, monoclonal, monovalent, humanized, human, bispecific, and heteroconjugate antibodies, are well known to skilled artisans.

Polyclonal Antibodies

Polyclonal antibodies can be produced in a mammal by injecting an immunogen alone or in combination with an adjuvant. Typically, the immunogen is injected in the mammal using one or more subcutaneous or intraperitoneal injections. The immunogen may include the polypeptide of interest or a fusion protein comprising the polypeptide and another polypeptide known to be immunogenic in the mammal being immunized. The immunogen may also include cells expressing a recombinant receptor or a DNA expression vector containing the receptor gene. Examples of such immunogenic proteins include, but are not limited to, keyhole limpet hemocyanin, serum albumin, bovine thyroglobulin, and soybean trypsin inhibitor. Examples of adjuvants include, but are not limited to, Freund's complete adjuvant and MPL-TDM adjuvant (monophosphoryl Lipid A, synthetic trehalose dicorynomycolate). The immunization protocol may be selected by one skilled in the art without undue experimentation.

Monoclonal Antibodies

Monoclonal antibodies can be produced using hybridoma methods such as those described by Kohler and Milstein, Nature, 256:495 (1975). In a hybridoma method, a mouse, rat, or other appropriate host mammal, is immunized with an immunogen to elicit lymphocytes that produce or are capable of producing antibodies that will specifically bind to the immunogen. Alternatively, the lymphocytes may be immunized in vitro. The immunogen will typically include the polypeptide of interest or a fusion protein containing such polypeptide. Generally, peripheral blood lymphocytes ("PBLs") cells are used if cells of human origin are desired. Spleen cells or lymph node cells are used if cells of non-human mammalian origin are desired. The lymphocytes are then fused with an immortalized cell line using a suitable fusing agent, e.g., polyethylene glycol, to form a hybridoma cell (Goding, Monoclonal Antibodies: Principles and Practice, pp 59-103 (Academic Press, 1986)). Immortalized cell lines are usually transformed mammalian cells, particularly rodent, bovine, or human myeloma cells. Usually, rat or mouse myeloma cell lines are employed. The hybridoma cells may be cultured in a suitable culture medium that preferably contains one or more substances that inhibit the growth or survival of the unfused immortalized cells. For example, if the parental cells lack the enzyme hypoxanthine guanine phosphoribosyl transferase (HGPRT), the culture medium for the hybridomas typically will include hypoxanthine, aminopterin, and thymidine (HAT medium). The HAT medium prevents the growth of HGPRT deficient cells.

Preferred immortalized cell lines are those that fuse efficiently, support stable high level expression of antibody by the selected antibody producing cells, and are sensitive to a medium such as HAT medium. More preferred immortalized cell lines are murine myeloma lines such as those derived from MOPC-21 and MPC-11 mouse tumors available from the Salk Institute Cell Distribution Center, San Diego, Calif. USA, and SP2/0 or X63-Ag8-653 cells available from the American Type Culture Collection, Rockville, Md. USA. Human myeloma and mouse-human heteromyeloma cell lines also have been described for use in the production of human monoclonal antibodies (Kozbor, J. Immunol. 133: 3001 (1984); Brodeur et al., Monoclonal Antibody Production Techniques and Applications, pp. 51-63 (Marcel Dekker, Inc., New York, 1987)). The mouse myeloma cell line NS0 may also be used (European Collection of Cell Cultures, Salisbury, Wiltshire UK). Human myeloma and mouse-human heteromyeloma cell lines, well known in the art, can also be used to produce human monoclonal antibodies.

The culture medium used for culturing hybridoma cells can then be assayed for the presence of monoclonal antibodies directed against the polypeptide of interest. Preferably, the binding specificity of monoclonal antibodies produced by the hybridoma cells is determined by immunoprecipitation or by an in vitro binding assay, e.g., radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980).

After the desired hybridoma cells are identified, the clones may be subcloned by limiting dilution procedures and grown by standard methods. Suitable culture media for this purpose include Dulbecco's Modified Eagle's Medium and RPMI-1640 medium. Alternatively, the hybridoma cells may be grown in vivo as ascites in a mammal.

The monoclonal antibodies secreted by the subclones are isolated or purified from the culture medium or ascites fluid by conventional immunoglobulin purification procedures such as protein G-Sepharose, protein A-Sepharose, hydroxylapatite chromatography, gel electrophoresis, dialysis, or affinity chromatography.

The monoclonal antibodies may also be produced by recombinant DNA methods, e.g., those described in U.S. Pat. No. 4,816,567. DNA encoding the monoclonal antibodies of the invention can be readily isolated and sequenced using conventional procedures, e.g., by using oligonucleotide probes that are capable of binding specifically to genes encoding the heavy and light chains of murine antibodies (Innis M. et al. In "PCR Protocols. A Guide to Methods and Applications", Academic, San Diego, Calif. (1990), Sanger, F. S, et al. Proc. Nat Acad. Sci. 74:5463-5467 (1977)). The hybridoma cells described herein serve as a preferred source of such DNA. Once isolated, the DNA may be placed into expression vectors. The vectors are then transfected into host cells such as simian COS cells, Chinese hamster ovary (CHO) cells, or myeloma cells that do not otherwise produce immunoglobulin protein. The recombinant host cells are used to produce the desired monoclonal antibodies. The DNA also may be modified, for example, by substituting the coding sequence for human heavy and light chain constant domains in place of the homologous murine sequences or by covalently joining the immunoglobulin coding sequence to all or part of the coding sequence for a non-immunoglobulin polypeptide. Such a non-immunoglobulin polypeptide can be substituted for the constant domains of an antibody or can be substituted for the variable domains of one antigen combining site of an antibody to create a chimeric bivalent antibody.

Monovalent antibodies can be produced using the recombinant expression of an immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking. Similarly, in vitro methods can be used for producing monovalent antibodies. Antibody digestion can be used to produce antibody fragments, preferably Fab fragments, using known methods.

Antibodies and antibody fragments can be produced using antibody phage libraries generated using the techniques described in McCafferty, et al., Nature 348:552-554 (1990). Clackson, et al., Nature 352:624-628 (1991) and Marks, et al., J. Mol. Biol. 222:581-597 (1991) describe the isolation of murine and human antibodies, respectively, using phage libraries. Subsequent publications describe the production of high affinity (nM range) human antibodies by chain shuffling (Marks, et al., Bio/Technology 10:779-783 (1992)), as well as combinatorial infection and in vivo recombination as a strategy for constructing very large phage libraries (Waterhouse, et al., Nuc. Acids. Res. 21:2265-2266 (1993)). Thus, these techniques are viable alternatives to traditional monoclonal antibody hybridoma techniques for isolation of monoclonal antibodies. Also, the DNA may be modified, for example, by substituting the coding sequence for human heavy-chain and light-chain constant domains in place of the homologous murine sequences (U.S. Pat. No. 4,816,567; Morrison, et al., Proc. Nat. Acad. Sci. USA 81:6851 (1984)), or by covalently joining to the immunoglobulin coding sequence all or part of the coding sequence for a non-immunoglobulin polypeptide. Typically, such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Antibodies can also be produced using electrical fusion rather than chemical fusion to form hybridomas. This technique is well established. Instead of fusion, one can also transform a B-cell to make it immortal using, for example, an Epstein Barr Virus, or a transforming gene "Continuously Proliferating Human Cell Lines Synthesizing Antibody of Predetermined Specificity," Zurawaki, V. R et al, in "Monoclonal Antibodies," ed. by Kennett R. H. et al, Plenum Press, N.Y. 1980, pp 19-33.

Humanized Antibodies

Humanized antibodies can be produced using the method described by Winter in Jones et al., Nature, 321:522-525 (1986); Riechmann et al., Nature, 332:323-327 (1988); and Verhoeyen et al., Science, 239:1 534-1536 (1988). Humanization is accomplished by substituting rodent complementary determining regions ("CDRs") or CDR sequences for the corresponding sequences of a human antibody. Generally, a humanized antibody has one or more amino acids introduced into it from a source that is non-human. Such "humanized" antibodies are chimeric antibodies wherein substantially less than an intact human variable domain has been substituted by the corresponding sequence from a non-human species. In practice, humanized antibodies are typically human antibodies in which some CDR residues and possibly some framework ("FR") residues are substituted by residues from analogous sites in rodent antibodies. Humanized forms of non-human (e.g., murine or bovine) antibodies are chimeric immunoglobulins, immunoglobulin chains, or immunoglobulin fragments such as Fv, Fab, Fab', F(ab')$_2$, or other antigen-binding subsequences of antibodies that contain minimal sequence derived from non-human immunoglobulin. Humanized antibodies include human immunoglobulins (recipient antibody) wherein residues from a complementary determining region (CDR) of the recipient are replaced by residues from a CDR of a non-human species (donor antibody) such as mouse, rat, or rabbit having the desired specificity, affinity, and capacity. Sometimes, Fv framework residues of the human immunoglobulin are replaced by corresponding non-human residues. Humanized antibodies also comprise residues that are found neither in the recipient antibody nor in the imported CDR or framework sequences. In general, humanized antibodies comprise substantially all of at least one and typically two variable domains wherein all or substantially all of the CDR regions correspond to those of a non-human immunoglobulin and all or substantially all of the FR regions are those of a human immunoglobulin consensus sequence. Humanized antibodies optimally comprise at least a portion of an immunoglobulin constant region (Fc), typically that of a human immunoglobulin.

Human Antibodies

Human antibodies can be produced using various techniques known in the art, e.g., phage display libraries as described in Hoogenboom and Winter, J. Mol. Biol., 227:381 (1991) and Marks et al., J. Mol. Biol., 222:581 (1991). Human monoclonal antibodies can be produced using the techniques described in Cole et al., Monoclonal Antibodies and Cancer Therapy, Alan R. Liss, p. 77 (1985) and Boemer et al., J. Immunol., 147(1):86-95 (1991). Alternatively, transgenic animals, e.g., mice, are available which, upon immunization, can produce a full repertoire of human antibodies in the absence of endogenous immunoglobulin production. Such transgenic mice are available from Abgenix, Inc., Fremont, Calif., and Medarex, Inc., Annandale, N.J. It has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA 90:2551 (1993); Jakobovits et al., Nature 362:255-258 (1993); Bruggermann et al., Year in Immunol. 7:33 (1993); and Duchosal et al. Nature 355:258 (1992). Human antibodies can also be derived from phage-display libraries (Hoogenboom et al., J. Mol. Biol. 227:381 (1991); Marks et al., J. Mol. Biol. 222:581-597 (1991); Vaughan, et al., Nature Biotech 14:309 (1996)).

Bispecific Antibodies

Bispecific antibodies can be produced by the recombinant co-expression of two immunoglobulin heavy-chain/light-chain pairs wherein the two heavy chains have different specificities. Bispecific antibodies are monoclonal, preferably human or humanized, antibodies that have binding specificities for at least two different antigens. In the present invention, one of the binding specificities is for a complement component and the other is for a CD14 pathway component Generally, the complement inhibitor of the present invention is an anti-complement component binding site on a bispecific antibody and the CD14 pathway inhibitor of the present invention is an anti-CD14 component binding site on a bispecific antibody. Preferably, a bispecific antibody has one binding specificity for C5a and another for CD14, although numerous other combinations are contemplated as part of the present invention. Because of the random assortment of immunoglobulin heavy and light chains, these hybridomas produce a potential mixture of ten different antibodies. However, only one of these antibodies has the correct bispecific structure. The recovery and purification of the correct molecule is usually accomplished by affinity chromatography.

Antibody variable domains with the desired binding specificities (antibody-antigen combining sites) can be fused to immunoglobulin constant domain sequences. The fusion preferably is with an immunoglobulin heavy chain constant domain comprising at least part of the hinge, CH2, and CH3 regions. Preferably, the first heavy-chain constant region (CH1) containing the site necessary for light-chain binding is present in at least one of the fusions. DNAs encoding the immunoglobulin heavy-chain and, if desired, the immunoglobulin light chain is inserted into separate expression vectors and co-transfected into a suitable host organism. Suitable techniques are shown in for producing bispecific antibodies are described in Suresh et al., Methods in Enzymology, 121:210 (1986).

Heteroconjugate Antibodies

Heteroconjugate antibodies can be produced using known protein fusion methods, e.g., by coupling the amine group of one an antibody to a thiol group on another antibody or other polypeptide. If required, a thiol group can be introduced using known methods. For example, immunotoxins comprising an antibody or antibody fragment and a polypeptide toxin can be produced using a disulfide exchange reaction or by forming a thioether bond. Examples of suitable reagents for this purpose include iminothiolate and methyl-4-mercaptobutyrimidate. Such antibodies can be used to target immune complement components and to prevent or treat sepsis.

The complement inhibitors and CD14 pathway inhibitors can be administered to the patient by any means that enables the inhibitor to reach the targeted cells. These methods include, but are not limited to, oral, rectal, nasal, topical, intradermal, subcutaneous, intravenous, intramuscular, intratrachehal, and intraperitoneally modes of administration. In one embodiment, the inhibitors are administered by placing the inhibitors directly into the lungs, typically by inhalation or tracheal instillation. Parenteral injections are preferred because they permit precise control of the timing and dosage levels used for administration. For parenteral administration, the complement inhibitors can be, for example, formulated as a solution, suspension, emulsion or lyophilized powder in association with a physiologically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

In another aspect, the present invention provides a composition useful for preventing and treating sepsis comprising one or more complement inhibitors, one or more CD14 pathway inhibitors, and preferably one or more pharmaceutically acceptable adjuvants, carriers, excipients, and/or diluents. Acceptable adjuvants, carriers, excipients, and/or diluents for making pharmaceutical compositions are well known to skilled artisans, e.g., Hoover, John E., Remington's Pharmaceutical Sciences, Mack Publishing Co., Easton, Pa. 1975. Another discussion of drug formulations can be found in Liberman, H. A. and Lachman, L., Eds., Pharmaceutical Dosage Forms, Marcel Decker, New York, N.Y., 1980. Most preferably, the inhibitors are mixed with pharmaceutically acceptable carriers to form a composition that allows for easy dosage preparation and administration. Aqueous vehicles prepared from water having no nonvolatile pyrogens, sterile water, and bacteriostatic water and containing at least 0.025M buffer salts, such as sodium phosphate, sodium bicarbonate, sodium citrate, etc. are also suitable to form injectable complement inhibitor solutions. In addition to these buffers, several other aqueous vehicles can be used. These include isotonic injection compositions that can be sterilized such as sodium chloride, Ringer's, dextrose, dextrose and sodium chloride, and lactated Ringer's. Addition of water-miscible solvents, such as methanol, ethanol, or propylene glycol generally increases solubility and stability of the inhibitors in these vehicles. Nonaqueous vehicles such as cottonseed oil, sesame oil, or peanut oil and esters such as isopropyl myristate may also be used as suspension vehicles for the inhibitors. Additionally, various additives which enhance the stability, sterility, and isotonicity of the composition including antimicrobial preservatives, antioxidants, chelating agents, and buffers can be added. Any vehicle, diluent, or additive used would, however, have to be biocompatible and compatible with the inhibitors according to the present invention.

When the complement inhibitor or CD14 pathway inhibitor is an antibody or antibody fragment, the formulation is any known formulation suitable for administering antibodies to a patient, e.g., solid antibody formulations such as those disclosed in US Patent Application No. 20020136719, reconstituted lyophilized formulations such as those disclosed in U.S. Pat. No. 6,267,958 or aqueous formulations such as those disclosed in U.S. Pat. No. 6,171,586.

The amount or dosage of complement inhibitor or CD14 pathway inhibitor administered to a patient varies depending upon patient type, patient age, patient size, inhibitor type, treatment frequency, administration purpose (therapeutic or prophylactic), and sepsis severity. Generally, the complement inhibitors are administered to the patient in dosages of from about 1 to 50 milligrams per kilogram of body weight (mg/kg) per day, preferably from about 5 to 30 mg/kg/day. When administered by inhalation or tracheal instillation, the complement inhibitors are administered to the patient in dosages of from about 0.5 to 20 mg/kg twice daily. Generally, the CD14 pathway inhibitors are administered to the patient in dosages of from about 10 to 200 milligrams per kilogram of body weight (mg/kg) per day, preferably from about 25 to 100 mg/kg/day. When administered by inhalation or tracheal instillation, the CD14 pathway inhibitors are administered to the patient in dosages of from about 1 to 40 mg/kg twice daily. The complement inhibitors can be administered in one dose or the dose can be broken up into smaller doses that can be administered more frequently.

In a preferred embodiment, a mixture of anti-C5a antibody and anti-CD14 antibody containing about 25 mg/kg anti-C5a and about 40 mg/kg of anti-CD14 is administered daily to a patient to prevent or treat sepsis. Similarly, the mixture can contain about 40 mg/kg anti-LPS antibody instead of anti-CD14 antibody.

Since the complement inhibitors and CD14 pathway inhibitors can be administered separately, the present invention also provides in another aspect an article of manufacture in the form of a kit for administering a sepsis preventing or treating composition to a patient comprising in separate containers in a single package a complement inhibitor and a CD14 pathway inhibitor. The kit contains the complement inhibitor in amounts sufficient to supply from about 25 mg/kg/day complement inhibitor and the CD14 pathway inhibitor in amounts sufficient to supply from about 40 mg/kg/day CD14 pathway inhibitor when administered to a patient.

EXAMPLES

This invention can be further illustrated by the following examples of preferred embodiments thereof, although it will be understood that these examples are included merely for purposes of illustration and are not intended to limit the scope of the invention unless otherwise specifically indicated.

Materials and Methods

Equipment: All equipment and solutions used were endotoxin-free according to information from the manufacturers. Polypropylene tubes were used to obtain low background activation of complement.

Reagents: Sterile phosphate-buffered saline (PBS) was obtained from Life Technologies (Paisley, UK), Lepirudin (Refludan®) was obtained from Hoechst (Frankfurt am Main, Germany). Opsonized *E. coli*, $1\times10^9$ bacteria/mL was obtained from ORPEGEN Pharma (Heidelberg, Germany); total endotoxin concentration in the *E. coli* suspension was 7 µg/mL when analyzed using the limulus amebocyte lysate assay. Mouse anti-human C5/C5a mAb 137-26 (purified IgG1) was generated by Tanox, Inc. (Houston, Tex.). Mouse anti-human CD14 mAb 18D11 (purified IgG1) was obtained from Diatec AS (Oslo, Norway) and its F(ab')$_2$ prepared by pepsin digestion. Cobra venom factor (CVF) was obtained commercially from Quidel. Bacterial lipopolysaccharide (LPS) was obtained commercially from Hoechst. Mouse anti-human CD11b PE conjugate was obtained from Becton Dickinson (San Jose, Calif.). Nuclear dye LDS-751 was obtained from Molecular Probes (Eugene, Oreg.).

Example 1

Complement Activation by *E. coil* but not LPS in a Human Whole Blood Model of Inflammation A human whole-blood model was used in the study as described in detail earlier (Mollnes T E et al. Blood 2002; 100: 1869-1877). The blood was collected from healthy volunteers and anticoagulated with lepirudin. Lepirudin was tested not to interfere with complement activation. The effects of *E. coli* ($1\times10^8$/mL), sonicated *E. coli* ($1\times10^8$/mL) and LPS (0.5 µg/mL) on complement activation in this system were tested. CVF (5 U/mL) was used as control for fluid-phase complement activation. All incubations were performed at 37° C. Plasma terminal sC5b-9 complex (TCC) formed as a result of complement activation was determined by enzyme-linked immunoassays (ELISAs) described in detail (Mollnes T E et al., Scand. J. Immunol. 1985; 22: 197-202). In this assay, a mAb specific to TCC was coated on the surface of wells in microtest plates. After sample incubation, immobilized TCC was detected by a biotinylated mouse mAb to human C6. Then streptavidin conjugated horseradish peroxidase was added for color development with substrate. The optical density (OD) of the reaction product was read with an ELISA plate reader at 450 nm. The results are shown in Table 1.

TABLE 1

TCC Formation (in arbitrary units/mL) in Human Whole Blood Induced by *E. coli* but not LPS

| | mAb 137-26 | | | |
|---|---|---|---|---|
| | 0 | 1 | 10 | 100 |
| Baseline | 0.2 | | | |
| Spontaneous | 1.2 | | | |
| +*E. coli* (1 × $10^8$/mL) | 64 | 48 | 101 | 65 |
| +Sonicated *E. coli* (1 × $10^8$/mL) | 55 | 53 | 88 | 56 |
| +LPS (0.5 µg/mL) | 2.1 | 2.6 | 8.7 | 5.7 |
| +CVF (5 U/mL) | 235 | 235 | 525 | 800 |

Referring to Table 1, the data show that *E. coli* but not LPS induced complement activation and TCC formation. mAb 137-26 did not inhibit fluid-phase TCC formation induced by *E. coli*. CVF induced fluid-phase TCC formation (via the activation of the alternative complement pathway). Taken together, the results show that whole bacteria (such as *E. coli*) activate complement, whereas endotoxin (LPS) derived from whole bacteria does not Thus, two distinct mechanisms of inflammation are triggered by bacteremia and endotoxemia in sepsis.

Example 2

Distinct Activation Pathways of Granulocytes and Monocytes Exposed to *E. coli* or LPS The whole blood system described in Example 1 was also used to study the activation of granulocytes and monocytes by *E. coli* (through C5a formed via complement activation) and LPS (through activation of CD14 pathway). Upregulation of CD11b was used as the indicator of activation of granulocytes and monocytes. Blood samples were preincubated for 4 minutes with anti-C5/C5a mAb 137-26, anti-CD14 18D11 F(ab')$_2$, a combination of mAb 137-26 and anti-CD14 18D11 F(ab')$_2$ or PBS. *E. coli* (1×$10^7$ bacteria/mL), or sonicated *E. coli* (1×$10^7$ bacteria/mL, LPS (0.5 µg/mL) or CVF (5 U/mL)) was added to test samples. PBS was used instead as negative control. The baseline sample was processed immediately before the addition of the activators. After incubation for 10 minutes at 37° C., 100 µL of blood was used for flow cytometric assays. The whole blood sample was fixed with paraformaldehyde and then stained with anti-CD11b PE and the nuclear dye LDS-751 (Molecular Probes, Inc., Eugene, Oreg.) CD11b expression was measured as median fluorescence intensity (MFI) using a FACSCalibur flow cytometer (Becton Dickinson, San José, Calif.). All experiments were performed 3-5 times. The results are shown in Table 2 and Table 3.

TABLE 2

Inhibition of C5a-induced CD11b Upregulation (in median fluorescence intensity) by Anti-C5/C5a mAb 137-26 in a Human Whole Blood Model

| | | Anti-C5/C5a mAb 137-26 (µg/mL) | | | |
|---|---|---|---|---|---|
| | | 0 | 1 | 10 | 100 |
| Granulocyte | Baseline | 59 | | | |
| | Spontaneous | 74 | | | |
| | +*E. coli* (1 × $10^8$/mL) | 2091 | 1640 | 1009 | 621 |
| | +Sonicated *E. coli* (1 × $10^8$/mL) | 1972 | 1582 | 806 | 661 |
| | +LPS (0.5 µg/mL) | 121 | 67 | 71 | 70 |
| | +CVF (5 U/mL) | 1023 | 667 | 64 | 67 |
| Monocyte | Baseline | 74 | | | |
| | Spontaneous | 97 | | | |
| | +*E. coli* (1 × $10^8$/mL) | 1670 | 1389 | 1420 | 1346 |
| | +Sonicated *E. coli* (1 × $10^8$/mL) | 1568 | 1512 | 1414 | 1407 |
| | +LPS (0.5 µg/mL) | 982 | 866 | 820 | 835 |
| | +CVF (5 U/mL) | 898 | 580 | 103 | 141 |

TABLE 3

Inhibition of CD11b Upregulation (in median fluorescence intensity) by Anti-C5/C5a mAb 137-26 and Anti-CD14 18D11 F(ab')$_2$ in a Human Whole Blood Model

| | | Anti-CD14 (µg/mL) | | | | Anti-C5/C5a (µg/mL) | | Anti-CD14 + Anti-C5/C5a (µg/mL) | |
|---|---|---|---|---|---|---|---|---|---|
| | | 0 | 4 | 20 | 40 | 0 | 25 | 0 | 25/20 |
| Granulocyte | Baseline | 44 | | | | | | | |
| | Spontaneous | 47 | | | | | | | |
| | +*E. coli* (1 × $10^8$/mL) | 1472 | 1207 | 1240 | 1269 | 1472 | 337 | 1472 | 62 |
| | +*E. coli* (4 × $10^6$/mL) | 178 | | | | 178 | 48 | 178 | 45 |
| | +LPS (0.5 µg/mL) | 43 | 43 | 49 | 54 | 43 | 41 | 43 | 43 |
| Monocyte | Baseline | 68 | | | | | | | |
| | Spontaneous | 68 | | | | | | | |
| | +*E. coli* (1 × $10^8$/mL) | 874 | 638 | 562 | 632 | 874 | 750 | 874 | 84 |
| | +*E. coli* (4 × $10^6$/mL) | 509 | | | | 509 | 496 | 509 | 62 |
| | +LPS (0.5 µg/mL) | 485 | 68 | 67 | 81 | 485 | 463 | 485 | 70 |

Referring to Table 2 and Table 3, the data show that *E. coli* activates granulocytes and monocytes, whereas LPS activates only monocytes. Anti-C5/C5a mAb 137-26 inhibits effectively in a dose-dependent manner granulocyte activation induced by *E. coli*, but it had only moderate inhibitory effect on monocyte activation. mAb 137-26 did not have any significant inhibitory effect on LPS-induced monocyte activation. The control CVF, which activated complement, induced activation of both neutrophils and monocytes. The activation was effectively inhibited by mAb 137-26. Anti-CD14 F(ab')$_2$ had minimal effect on granulocyte and monocyte activation induced by *E. coli* (Table 3). In contrast, it inhibited effectively LPS-induced monocyte activation. The combination of anti-CD14 F(ab')$_2$ and anti-C5/C5a mAb 137-26 achieved complete inhibition of neutrophil and monocyte activation induced by either *E. coli* or LPS.

Collectively, the results from Tables 2 and Table 3 indicate that *E. coli* (bacteremia) induced C5a production through complement activation and thus activates predominantly granulocytes and to a less extent monocytes, whereas bacterial LPS activates mainly monocytes through a CD14-dependent pathway which is independent of complement. Therefore, administering a combination of complement inhibitors and CD14 pathway inhibitors to a patient can be used as a method for preventing or treating sepsis.

In the specification, there have been disclosed typical preferred embodiments of the invention and, although specific terms are employed, they are used in a generic and descriptive sense only and not for purposes of limitation, the scope of the invention being set forth in the following claims. Obviously many modifications and variations of the present invention are possible in light of the above teachings. It is therefore to be understood that within the scope of the appended claims the invention may be practiced otherwise than as specifically described.

What is claimed is:

1. A composition for administration to a patient in need thereof for the prevention or treatment of sepsis comprising a complement inhibitor, and a CD14 pathway inhibitor,
   wherein the complement inhibitor is an anti-C5a antibody or a binding fragment thereof,
   wherein the CD14 pathway inhibitor is an anti-CD14 antibody or a binding fragment thereof,
   wherein the sepsis is induced by gram negative bacteria, and
   wherein the composition can be administered by oral, rectal, nasal, topical, intradermal, subcutaneous, intravenous, intramuscular, intratracheal, or intraperitoneal means.

2. The composition of claim 1, wherein said anti-CD14 antibody has altered effector functions of the Fc region.

3. A composition for administration to a patient in need thereof for the prevention or treatment of sepsis, comprising a bispecific antibody comprising a first binding element that binds C5a and a second binding element that binds CD14,
   wherein the sepsis is induced by gram negative bacteria, and
   wherein the composition can be administered by oral, rectal, nasal, topical, intradermal, subcutaneous, intravenous, intramuscular, intratracheal, or intraperitoneal means.

4. The composition of claim 1 or 3, further comprising one or more pharmaceutically acceptable adjuvants, carriers, excipients, and/or diluents.

5. A kit for administration to a patient in need thereof for the prevention or treatment of sepsis, comprising a complement inhibitor and a CD14 pathway inhibitor, in separate containers,
   wherein the complement inhibitor is an anti-C5a antibody or a binding fragment thereof,
   wherein the CD14 pathway inhibitor is an anti-CD 14 antibody or a binding fragment thereof,
   wherein the sepsis is induced by gram negative bacteria, and
   wherein the complement inhibitor and CD14 pathway inhibitor can be administered by oral, rectal, nasal, topical, intradermal, subcutaneous, intravenous, intramuscular, intratracheal, or intraperitoneal means.

6. The kit of claim 5, wherein the amount of said complement inhibitor or CD 14 pathway inhibitor is sufficient for dosages of 1 to 200 milligrams per kilogram of body weight per day.

7. The composition of claim 1, wherein the amount of said complement inhibitor or CD 14 pathway inhibitor is sufficient for dosages of 1 to 200 milligrams per kilogram of body weight per day.

8. The composition of claim 3, wherein the amount of the bispecific antibody is sufficient for dosages of 1 to 200 milligrams per kilogram of body weight per day.

9. The kit of claim 5, wherein the anti-CD14 antibody has altered effector functions of the Fc region.

10. The composition of claim 1 or 3, wherein the composition is for the prevention of sepsis.

11. The composition of claim 1 or 3, wherein the composition is for the treatment of sepsis.

12. The kit of claim 5, wherein the kit is for the prevention of sepsis.

13. The kit of claim 5, wherein the kit is for the treatment of sepsis.

* * * * *